(12) United States Patent
Sun et al.

(10) Patent No.: US 11,986,575 B2
(45) Date of Patent: May 21, 2024

(54) PREPARATION METHOD OF ABSORBABLE VASCULAR STENT COATING FOR ANGIOSTENOSIS IN INFANT

(71) Applicant: XINHUA HOSPITAL AFFILIATED TO SHANGHAI JIAOTONG UNIVERSITY SCHOOL OF MEDICINE, Shanghai (CN)

(72) Inventors: Kun Sun, Shanghai (CN); Jing Sun, Shanghai (CN); Sun Chen, Shanghai (CN); Kai Bai, Shanghai (CN); Yanan Lu, Shanghai (CN); Lu Wang, Shanghai (CN); Fujun Wang, Shanghai (CN); Fan Zhao, Shanghai (CN); Jihong Huang, Shanghai (CN)

(73) Assignee: XINHUA HOSPITAL AFFILIATED TO SHANGHAI JIAOTONG UNIVERSITY SCHOOL OF MEDICINE, Shanghai (CN)

( * ) Notice: Subject to any disclaimer, the term of this patent is extended or adjusted under 35 U.S.C. 154(b) by 0 days.

(21) Appl. No.: 18/280,275

(22) PCT Filed: Mar. 29, 2022

(86) PCT No.: PCT/CN2022/083531
§ 371 (c)(1),
(2) Date: Sep. 5, 2023

(87) PCT Pub. No.: WO2022/184183
PCT Pub. Date: Sep. 9, 2022

(65) Prior Publication Data
US 2024/0042109 A1    Feb. 8, 2024

(30) Foreign Application Priority Data
Mar. 5, 2021   (CN) .......................... 202110246916.5

(51) Int. Cl.
  *A61L 31/16*   (2006.01)
  *A61L 31/10*   (2006.01)
  *A61L 31/14*   (2006.01)

(52) U.S. Cl.
  CPC .............. *A61L 31/16* (2013.01); *A61L 31/10* (2013.01); *A61L 31/148* (2013.01);
  (Continued)

(58) Field of Classification Search
  CPC ..................................................... A61L 31/16
  See application file for complete search history.

(56) References Cited

U.S. PATENT DOCUMENTS

2005/0175703 A1*  8/2005  Hunter .................... A61L 31/16
                                                              514/453
2017/0252494 A1    9/2017  Nagale et al.
(Continued)

FOREIGN PATENT DOCUMENTS

CN   103157132 A    6/2013
CN   104225683 A    12/2014
(Continued)

OTHER PUBLICATIONS

Dao-Lu Tang, et al., A pH-responsive chitosan-b-poly(p-dioxanone) nanocarrier: formation and efficient antitumor drug delivery, Nanotechnology, 2013, pp. 1-10, vol. 24, 145101.
(Continued)

*Primary Examiner* — Dah-Wei D. Yuan
*Assistant Examiner* — Andrew J Bowman
(74) *Attorney, Agent, or Firm* — Bayramoglu Law Offices LLC (57) ABSTRACT

A preparation method of drug-loaded micelles of an absorbable vascular stent coating for angiostenosis in an infant is provided, including the following steps: S1: dissolving a drug to be encapsulated in an appropriate amount of an
(Continued)

emulsifying agent, adding a chitosan-poly(p-dioxohone) amphiphilic block copolymer (chitosan-b-PPDO copolymer), and thoroughly mixing to obtain a drug-copolymer solution; S2: adding the drug-copolymer solution obtained in S1 dropwise to an emulsifying agent aqueous solution prepared in advance, and continuously stirring to obtain a stable drug-loaded micellar solution; and S3: removing the emulsifying agent from the micellar solution obtained in S2 through vacuum evaporation, stirring a resulting concentrate, and centrifuging the concentrate to obtain a supernatant; and filtering the supernatant to obtain a filtrate, and subjecting the filtrate to dialysis to obtain the drug-loaded micelles.

18 Claims, 1 Drawing Sheet

(52) U.S. Cl.
CPC ..... *A61L 2300/21* (2013.01); *A61L 2300/216* (2013.01); *A61L 2300/41* (2013.01); *A61L 2300/416* (2013.01); *A61L 2300/626* (2013.01); *A61L 2300/802* (2013.01); *A61L 2420/02* (2013.01); *A61L 2420/06* (2013.01)

(56) References Cited

U.S. PATENT DOCUMENTS

| | | |
|---|---|---|
| 2019/0290799 A1 | 9/2019 | Arshi et al. |
| 2020/0390932 A1 | 12/2020 | MacEwan |

FOREIGN PATENT DOCUMENTS

| | | |
|---|---|---|
| CN | 109701083 A | 5/2019 |
| CN | 108066048 B | 9/2019 |
| CN | 113018518 A | 6/2021 |
| EP | 2015792 A1 | 1/2009 |

OTHER PUBLICATIONS

Xiu-Li Wang, et al., Self-assembly, drug-delivery behavior, and cytotoxicity evaluation of amphiphilic chitosan-graft-poly (1,4-dioxan-2-one) copolymers, J Polym Res, 2012, pp. 1-9, vol. 19, 9946.

Xiu-Li Wang, et al., Chitosan-graft poly(p-dioxanone) copolymers: preparation, characterization, and properties, Carbohydrate Research, 2009, pp. 801-807, vol. 344.

* cited by examiner

PREPARATION METHOD OF ABSORBABLE VASCULAR STENT COATING FOR ANGIOSTENOSIS IN INFANT

CROSS REFERENCE TO THE RELATED APPLICATIONS

This application is the national phase entry of International Application No. PCT/CN2022/083531, filed on Mar. 29, 2022, which is based upon and claims priority to Chinese Patent Application No. 202110246916.5, filed on Mar. 5, 2021, the entire contents of which are incorporated herein by reference.

TECHNICAL FIELD

The present disclosure relates to the technical field of medicine, and specifically to a preparation method of an absorbable vascular stent coating for angiostenosis in an infant.

BACKGROUND

Percutaneous vascular stent implantation is less invasive and more curative than artificial vascular replacement and balloon dilation of blood vessels alone. Most experts and scholars believe that the use of an absorbable stent in an infant with angiostenosis has a high clinical research value, and can overcome many serious problems such as relative narrowing, repeated dilation, and thrombogenicity of a blood vessel implanted with a permanent metal stent in an infant after growing up, and it is extremely difficult to solve these problems. Research on absorbable stents has been widely conducted inside and outside China, but there is still a lack of absorbable stents designed for angiostenosis in infants.

Materials used for bioabsorbable stents are mostly polymers, including poly-L-lactic acid (PLLA), polyglycolide (PGA), poly(lactic-co-glycolic acid) (PLGA), poly(para-dioxanone) (PPDO), and polycaprolactone (PCL). These materials have different degradation times, and have different mechanical strengths to adapt to different vascular support requirements when prepared into vascular stents, and degradation products of these materials are safe and non-toxic and can be excreted through cell metabolism. The usual method for preparing a stent with a degradable polymer is as follows: the degradable polymer is first prepared into substrate fibers for the stent through melt spinning or solution casting, then wound into a designed stent shape on a mold, and heated for curing.

Research and analysis inside and outside China show that polymer absorbable stents are mostly suitable for small blood vessels (blood vessel diameter: 3 mm to 5 mm) such as coronary arteries in adults, have long degradation cycles mostly of 2 to 3 years, and need to be prepared by a complicated method with a high production cost; and polymer absorbable stents have lower radial support performance than the traditional metal stents, and cannot be used in infants. For example, CN108066048B discloses a preparation method of a degradable lumen stent with a thermally-bonded composite structure, including: woven yarns with a thermally-bonded PPDO/PCL skin-core structure are prepared and cross-woven with PPDO monofilaments to produce a stent preform, and then the stent preform is subjected to a heat-setting treatment to obtain a PPDO/PCL-woven self-reinforced vascular stent with a stable structure, where the thermally-bonded woven yarns can limit the slippage and rotation of some weaving points in a weaving structure to improve the mechanical performance of the stent. The stent can play an excellent vascular support role in a body within 4 months and can be completely degraded and fused with a vascular wall 12 months later, and the stent degradation can meet the requirements of vascular growth and development in an infant. However, the stent has poor biocompatibility at a middle stage of degradation (4 to 6 months), and stent inflammation and smooth muscle cell (SMC) proliferation are considered to be major factors for luminal restenosis of a polymer stent and may induce thrombosis and adverse vascular events, resulting in poor stent efficacy. Therefore, the development of a vascular stent that has a small initial volume (a length and a diameter meet the requirements) and excellent biocompatibility, needs to play a support role for at least 3 to 6 months to complete vascular repair, and can be completely degraded within 6 to 12 months to adapt to a vascular development rate of an infant is an urgent problem to be solved in the prior art.

SUMMARY

In order to overcome the defects in the prior art, the present disclosure designs and constructs a drug-loaded composite coating of an absorbable vascular stent suitable for angiostenosis in an infant to regulate the biocompatibility of the absorbable vascular stent. The present disclosure provides a novel drug release pathway, which does not affect the reendothelialization of a damaged blood vessel at an early stage of stent degradation and can release a drug at a middle stage of degradation to play anti-inflammation and anti-proliferation roles. The coating material of the present disclosure can be biodegraded after the release of a drug and does not increase an incidence of thrombosis at a late stage. Thus, the stent of the present disclosure as a whole can finally be completely biodegraded.

The present disclosure is implemented by the following technical solutions:

In a first aspect, the present disclosure provides a preparation method of a polymer drug-loaded micellar solution of an absorbable vascular stent coating for angiostenosis in an infant, including the following steps:

S1: dissolving a drug to be encapsulated in an appropriate amount of an emulsifying agent, adding a chitosan-poly(p-dioxohone) amphiphilic block copolymer (chitosan-b-PPDO copolymer), and thoroughly mixing to obtain a drug-copolymer solution, where a mass ratio of the drug to be encapsulated to the chitosan-b-PPDO copolymer is 10:(20-60), and preferably, the mass ratio of the drug to be encapsulated to the chitosan-b-PPDO copolymer is 10:25;

S2: adding the drug-copolymer solution obtained in S1 dropwise to an emulsifying agent aqueous solution prepared in advance, and continuously stirring for 12 h to 36 h to obtain a stable drug-loaded micellar solution, where a mass ratio of an emulsifying agent to water in the emulsifying agent aqueous solution is 1:(0.5-2), and preferably, the mass ratio of the emulsifying agent to the water in the emulsifying agent aqueous solution is 1:1; a mass of the drug-copolymer solution is 2% to 10% of a mass of the emulsifying agent aqueous solution, and preferably, the mass of the drug-copolymer solution is 3.5% of the mass of the emulsifying agent aqueous solution; and preferably, the continuous stirring is conducted for 24 h; and S3: removing the emulsifying agent from the drug-loaded micellar solution obtained in S2 through vacuum evaporation, stirring a resulting concentrate for 2 h to 4 h, and centrifuging the concentrate to obtain a supernatant; and filtering the supernatant to obtain a filtrate, and subjecting the filtrate to dialysis to completely remove the unbound copolymer and the residual emulsifying agent to obtain the polymer drug-loaded micellar solution, where preferably, the stirring is conducted for 3 h.

In a second aspect, the present disclosure provides a preparation method of a polymer blank micellar solution of an absorbable vascular stent coating for angiostenosis in an infant, including the following steps:

S1': dissolving a chitosan-b-PPDO copolymer in a small amount of an emulsifying agent to obtain a copolymer solution, adding the copolymer solution dropwise to an emulsifying agent aqueous solution prepared in advance, and continuously stirring for 12 h to 36 h to obtain a stable micellar solution, where a mass ratio of an emulsifying agent to water in the emulsifying agent aqueous solution is 1:(0.5-2), and preferably, the mass ratio of the emulsifying agent to the water in the emulsifying agent aqueous solution is 1:1; a mass of the copolymer solution is 2% to 10% of a mass of the emulsifying agent aqueous solution, and preferably, the mass of the copolymer solution is 3.5% of the mass of the emulsifying agent aqueous solution; and preferably, the continuous stirring is conducted for 24 h; and

S2': removing the emulsifying agent from the drug-loaded micellar solution obtained in S1' through vacuum evaporation, stirring a resulting concentrate for 2 h to 4 h, and centrifuging the concentrate to obtain a supernatant; and filtering the supernatant to obtain a filtrate, and subjecting the filtrate to dialysis to completely remove the unbound copolymer and the residual emulsifying agent to obtain the polymer drug-loaded micellar solution, where preferably, the stirring is conducted for 3 h.

Further, in S1, the drug is an anti-SMC proliferation drug and/or an anti-inflammatory drug.

Furthermore, the anti-SMC proliferation drug is rapamycin (RAPA).

Furthermore, the anti-inflammatory drug is ibuprofen.

Figure 1:
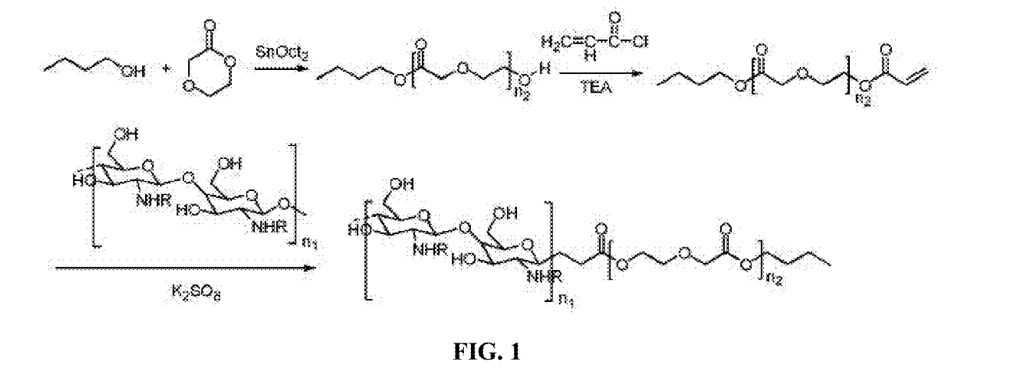
FIG. 1 shows a reaction equation of the present disclosure.
Figure 2:
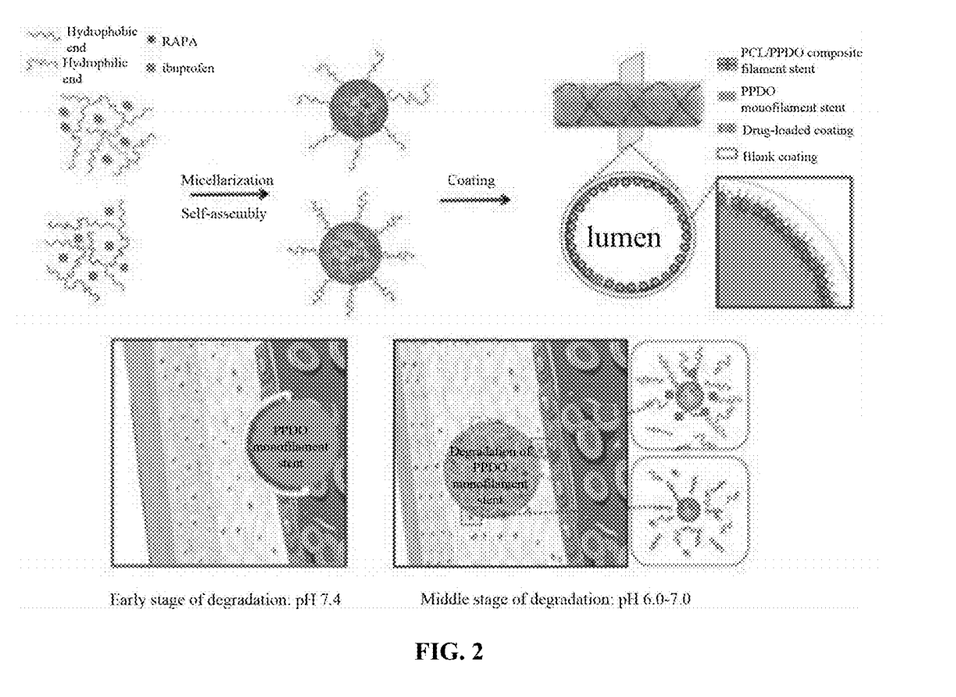
FIG. 2 is a schematic flow chart of preparation of the absorbable vascular stent in the present disclosure.

Further, in S1 and S1', the chitosan-b-PPDO copolymer is shown in formula I:

where R is H or $OCH_3$; and $n_1$ and $n_2$ each are a positive integer, and $n_1:n_2=1:(10\text{-}20)$.

Furthermore, a preparation method of the chitosan-b-PPDO copolymer includes the following steps:

where R is H or $OCH_3$; and $n_1$ and $n_2$ each are a positive integer, and $n_1:n_2=1:(10\text{-}20)$.

Further, the emulsifying agent is selected from the group consisting of acetone, dichloromethane (DCM), and chloroform.

Further, in S3 and S2', the vacuum evaporation is conducted at a temperature of 160° C. to 170° C. and a pressure of 1 mmHg to 3 mmHg; and preferably, in S3 and S2', the vacuum evaporation is conducted at a temperature of 165° C. and a pressure of 2 mmHg.

Further, in S3 and S2', the filtration is conducted with a microporous filter membrane.

Further, in S3 and S2', the dialysis is conducted by a dialysis bag with a molecular weight cut-off (MWCO) of 3,500 or more.

In a third aspect, the present disclosure also provides a polymer drug-loaded micellar solution of an absorbable vascular stent coating for angiostenosis in an infant, where the polymer drug-loaded micellar solution is prepared by the preparation method of a polymer drug-loaded micellar solution described above.

In a fourth aspect, the present disclosure also provides a polymer blank micellar solution of an absorbable vascular stent coating for angiostenosis in an infant, where the polymer blank micellar solution is prepared by the preparation method of a polymer blank micellar solution described above.

In a fifth aspect, the present disclosure also provides a spraying method of a drug-loaded micellar solution of an absorbable vascular stent coating for angiostenosis in an infant, including the following steps:

S1: preparation of a drug-loaded coating: uniformly spraying the polymer drug-loaded micellar solution as a spraying solution on a surface of an absorbable vascular stent by an ultrasonic spraying process to obtain an absorbable vascular stent with the drug-loaded coating, where preferably, the drug-loaded coating includes an RAPA-loaded coating and/or an ibuprofen-loaded coating; and more preferably, the drug-loaded coating includes an RAPA-loaded coating and an ibuprofen-loaded coating, and a ratio of a number of RAPA-loaded coatings to a number of ibuprofen-loaded coatings is 4:3; and S2: preparation of a blank coating: uniformly spraying the polymer blank micellar solution as a spraying solution on a surface of the absorbable vascular stent with the drug-loaded coating by an ultrasonic spraying process to obtain an absorbable vascular stent with the drug-loaded coating and the blank coating in which a ratio of a number of drug-loaded coatings to a number of blank coatings is 7:3.

Further, the ultrasonic spraying process in S1 includes:

S11: washing the absorbable vascular stent with an acid to remove impurities on the surface of the absorbable vascular stent, rinsing the absorbable vascular stent with ultrapure water (UPW) to remove the acid on the surface, vacuum-drying the absorbable vascular stent, and fixing the absorbable vascular stent on an automatic ultrasonic sprayer; and S12: loading the polymer drug-loaded micellar solution into a microsyringe pump, and ultrasonically spraying the polymer drug-loaded micellar solution uniformly on the surface of the absorbable vascular stent to obtain the absorbable vascular stent with the drug-loaded coating, where the ultrasonic spraying is conducted under the following conditions: ultrasonic power: 2 W to 5 W and preferably 3.5 W; flow rate of the microsyringe pump: 3 mL/h to 5 mL/h and preferably 4 mL/h; nitrogen pressure: 2 psi to 5 psi and preferably 3.5 psi; and rotational speed of a rotating mandrel: 100 rpm to 300 rpm and preferably 200 rpm.

Furthermore, S12 includes:

A: preparation of an RAPA-loaded coating: ultrasonically spraying a polymer RAPA-loaded micellar solution as a spraying solution uniformly on the surface of the absorbable vascular stent to obtain an absorbable vascular stent with the RAPA-loaded coating, where the ultrasonic spraying is conducted under the following conditions: ultrasonic power: 2 W to 5 W and preferably 3.5 W; flow rate of the microsyringe pump: 3 mL/h to 5 mL/h and preferably 4 mL/h; nitrogen pressure: 2 psi to 5 psi and preferably 3.5 psi; and rotational speed of a rotating mandrel: 100 rpm to 300 rpm and preferably 200 rpm; or B: preparation of an ibuprofen-loaded coating: ultrasonically spraying a polymer ibuprofen-loaded micellar solution as a spraying solution uniformly on the surface of the absorbable vascular stent to obtain an absorbable vascular stent with the ibuprofen-loaded coating, where the ultrasonic spraying is conducted under the following conditions: ultrasonic power: 2 W to 5 W and preferably 3.5 W; flow rate of the microsyringe pump: 3 mL/h to 5 mL/h and preferably 4 mL/h; nitrogen pressure: 2 psi to 5 psi and preferably 3.5 psi; and rotational speed of a rotating mandrel: 100 rpm to 300 rpm and preferably 200 rpm; or C: preparation of an RAPA-loaded coating and an ibuprofen-loaded coating: ultrasonically spraying a polymer RAPA-loaded micellar solution as a spraying solution uniformly on the surface of the absorbable vascular stent, and ultrasonically spraying a polymer ibuprofen-loaded micellar solution as a spraying solution uniformly on a surface of an absorbable vascular stent with the RAPA-loaded coating to obtain an absorbable vascular stent with the RAPA-loaded coating and the ibuprofen-loaded coating in which a ratio of a number of RAPA-loaded coatings to a number of ibuprofen-loaded coatings is 4:3, where the ultrasonic spraying is conducted under the following conditions: ultrasonic power: 2 W to 5 W and preferably 3.5 W; flow rate of the microsyringe pump: 3 mL/h to 5 mL/h and preferably 4 mL/h; nitrogen pressure: 2 psi to 5 psi and preferably 3.5 psi; and rotational speed of a rotating mandrel: 100 rpm to 300 rpm and preferably 200 rpm.

Further, the ultrasonic spraying process in S2 includes:

S21: washing the absorbable vascular stent with an acid to remove impurities on the surface of the absorbable vascular stent, rinsing the absorbable vascular stent with UPW to remove the acid on the surface, vacuum-drying the absorbable vascular stent, and fixing the absorbable vascular stent on an automatic ultrasonic sprayer; and S22: ultrasonically spraying the polymer blank micellar solution as a spraying solution uniformly on the surface of the absorbable vascular stent with the drug-loaded coating to obtain the absorbable vascular stent with the drug-loaded coating and the blank coating in which a ratio of a number of drug-loaded coatings to a number of blank coatings is 7:3, where the ultrasonic spraying is conducted under the following conditions: ultrasonic power: 2 W to 5 W and preferably 3.5 W; flow rate of the microsyringe pump: 3 mL/h to 5 mL/h and preferably 4 mL/h; nitrogen pressure: 2 psi to 5 psi and preferably 3.5 psi; and rotational speed of a rotating mandrel: 100 rpm to 300 rpm and preferably 200 rpm.

Beneficial Effects

When applied to a surface of a degradable and absorbable biological stent, the drug-loaded micellar coating prepared by the present disclosure has the following advantages: (1) The drug-loaded micellar coating does not affect the reendothelialization of a damaged blood vessel at an early stage of stent degradation and can release a drug at a middle stage of degradation to play anti-inflammation and anti-proliferation roles. The coating material can be biodegraded after the release of a drug and does not increase an incidence of thrombosis at a late stage, which allows the stent as a whole to be completely biodegraded and significantly improves the biocompatibility of the absorbable stent. (2) In a composite coating manner, drug-loaded micelles are first sprayed, and then drug-free blank micelles are sprayed, which allows the sustained drug release of pH-responsive drug-loaded micelles with a pH change during degradation of a stent skeleton and a blank top layer.

DETAILED DESCRIPTION OF THE EMBODIMENTS

The present disclosure is further described in detail below with reference to the accompanying drawings and specific embodiments.

In a specific embodiment, the stent used in the present disclosure is an absorbable vascular stent prepared by the preparation method disclosed in CN108066048B.

Example 1 Synthesis of a pH-Responsive Chitosan-b-PPDO Polymer

A para-dioxanone (PDO) monomer was added to a stannous octoate catalyst (a molar ratio of the $SnOct_2$ to the PDO was 1:10,000), a resulting mixture was placed in a reactor and then frozen with liquid nitrogen, and then the reactor was placed in an oil bath at 80° C. to allow a reaction for 48 h; then the reactor was cooled to 0° C., such that the reaction was stopped to obtain a hydroxyl-terminated PPDO monomer (OH-PPDO-BA); the OH-PPDO-BA was dissolved in acryloyl chloride (a molar ratio of the OH-PPDO-BA to the acryloyl chloride was 1:8), then triethylamine (TEA) was added as a catalyst at an equal molar amount to OH-PPDO-BA, and a reaction was conducted for 10 h at 25° C. in the dark; then diethyl ether was added to remove unreacted reagents, washing was conducted three times with deionized water to remove insoluble substances produced during the reaction, and a resulting product was vacuum-dried at 40° C. for 12 h to obtain allyl-terminated PPDO (allyl-PPDO-BA); 15 moles of chitosan ($Mn=8*10^5$, deacetylation degree: 100%) was dissolved in a 0.1 mol/L acetic acid aqueous solution, and under protection of an inert gas, $K_2SO_8$ (KPS) was added, and a resulting mixture was stirred at 25° C. for 20 min; 85 moles of the allyl-PPDO-BA was then added, and a copolymerization reaction was conducted at 50° C. for 2 h; and a resulting product was washed with acetone and deionized water to remove unreacted homopolymers, and then cooled to obtain the chitosan-b-PPDO copolymer (molecular weight Mn=3,100 g/mol). A copolymerization site is localized on a radical of chitosan while retaining free amino on a main chain of chitosan. At a middle stage of degradation of a stent, a degradation product of a PPDO chain accumulates, such that a local pH around the stent is reduced to form an acidic microenvironment; and because chitosan has amino, an acid-base dissociation degree pKa of chitosan is 6.3 to 7.0 (20° C.) and is just between a pH of blood (pH 7.4) and a pH of a PPDO-degrading acidic microenvironment (pH 6.0-7.0), such that amino of chitosan is protonated, and a micellar structure changes and expands to promote the release of a drug encapsulated at a hydrophobic end, thereby enabling a function of pH-responsive micelles.

A block site is located on a radical of chitosan while retaining free amino on a main chain of chitosan, thereby enabling pH sensitivity. In general, a content of hydrophobic groups in the amphiphilic copolymer and a molecular weight of the copolymer will greatly affect a particle size of self-assembled nanomicelles of the copolymer. In this experiment, a molecular weight of PPDO microspheres was controlled to prepare polymer 1 (chitosan-b-PPDO940 (Mn=3,100)) and polymer 2 (chitosan-b-PPDO2000 (Mn=6, 200)).

Example 2 Preparation of Polymer Drug-Loaded Micelles

S1: A drug to be encapsulated (ibuprofen/10 mg or RAPA/10 mg) was dissolved in 3.5 mL of a solvent (anhydrous chloroform, acetone, or DCM), then 25 mg of the chitosan-b-PPDO synthesized in Example 1 (polymer 1 and polymer 2) was added, and a resulting mixture was thoroughly mixed for dissolution to obtain a drug-copolymer solution.

S2: The drug-copolymer solution obtained in S1 was added dropwise to an emulsifying agent aqueous solution prepared in advance, and a resulting mixture was continuously stirred for 24 h to obtain a stable drug-loaded micellar solution, where a mass ratio of an emulsifying agent to water in the emulsifying agent aqueous solution was 1:1, and a mass of the drug-copolymer solution was 3.5% of a mass of the emulsifying agent aqueous solution.

S3: The emulsifying agent was removed from the drug-loaded micellar solution through vacuum evaporation, and a resulting concentrate was stirred for 3 h and centrifuged to obtain a supernatant; and the supernatant was filtered through a 0.22 m filter membrane and then subjected to dialysis by a dialysis membrane with an MWCO of 3,500 to remove the unbound copolymer and the residual emulsifying agent and solvent to obtain a polymer drug-loaded micellar solution.

Example 3 Preparation of Blank Micelles

S1: The chitosan-b-PPDO copolymer was dissolved in a small amount of an emulsifying agent to obtain a copolymer solution, then the copolymer solution was added dropwise to an emulsifying agent aqueous solution prepared in advance, and a resulting mixture was continuously stirred for 24 h to obtain a stable blank micellar solution, where a mass ratio of an emulsifying agent to water in the emulsifying agent aqueous solution was 1:1, and a mass of the copolymer solution was 3.5% of a mass of the emulsifying agent aqueous solution.

S2: The emulsifying agent was removed from the blank micellar solution through vacuum evaporation, and a resulting concentrate was stirred for 3 h and centrifuged to obtain a supernatant; and the supernatant was filtered through a 0.22 m filter membrane and then subjected to dialysis by a dialysis membrane with an MWCO of 3,500 to remove the unbound copolymer and the residual emulsifying agent and solvent to obtain a polymer blank micellar solution.

Dynamic light scattering (DLS) was used to determine a particle size (D) and a distribution (dispersion coefficient PDI) of drug-loaded micelles, and high-performance liquid chromatography (HPLC) was used to determine a drug loading rate (LC, %) and an encapsulation rate (EE, %) of micelles. Results were shown in Table 1. Compared with polymer microspheres without RAPA, a particle size of polymer microspheres with RAPA is significantly increased, indicating that RAPA is encapsulated in the polymer microspheres. In addition, it can be seen that a particle size of polymer 1-blank microspheres is slightly larger than a particle size of polymer2-blank microspheres, which is due to poor crystallization performance of short PPDO chains, loose cores of micelles, and increased micelle volumes; after drug loading, a difference between the particle sizes of the two was not significant, and was about 170 nm; and the two drug-loaded microspheres have both a low drug loading rate and a low encapsulation rate.

TABLE 1

Characterization results of the chitosan-b-PPDO copolymer

| Polymer | Blank microspheres | | Drug-loaded microspheres | | | |
|---|---|---|---|---|---|---|
| | D (nm) | PDI | D (nm) | PDI | LC (%) | EE (%) |
| Polymer 1 | 135 | 0.15 | 175 | 0.16 | 24 | 60 |
| Polymer 2 | 85 | 0.11 | 170 | 0.23 | 21 | 64 |

Example 4 Preparation Method of a Stent with a Drug (RAPA)-Loaded Coating

A spraying method of drug-loaded micelles of an absorbable vascular stent coating for angiostenosis in an infant was provided, including the following steps:

S1: Preparation of drug-loaded coatings: S11: An absorbable vascular stent was washed with an acid to remove impurities on a surface of the absorbable vascular stent, then rinsed with UPW to remove the acid on the surface, vacuum-dried, and fixed on an automatic ultrasonic sprayer. S12: A polymer RAPA-loaded micellar solution was ultrasonically sprayed as a spraying solution uniformly on the surface of the absorbable vascular stent 7 times to obtain an absorbable vascular stent with RAPA-loaded coatings, where the ultrasonic spraying was conducted under the following conditions: ultrasonic power: 3.5 W, flow rate of a microsyringe pump: 4 mL/h, nitrogen pressure: 3.5 psi, and rotational speed of a rotating mandrel: 200 rpm.

S2: Preparation of blank coatings: S21: The absorbable vascular stent with RAPA-loaded coatings prepared in S1 was washed with an acid to remove impurities on a surface of the absorbable vascular stent, then rinsed with UPW to remove the acid on the surface, vacuum-dried, and fixed on an automatic ultrasonic sprayer. S22: A polymer blank micellar solution was loaded into a microsyringe pump and ultrasonically sprayed uniformly on the surface of the absorbable vascular stent with RAPA-loaded coatings prepared in S21 3 times to obtain an absorbable vascular stent with RAPA-loaded coatings and blank coatings, where the ultrasonic spraying was conducted under the following conditions: ultrasonic power: 3.5 W, flow rate of the microsyringe pump: 4 mL/h, nitrogen pressure: 3.5 psi, and rotational speed of a rotating mandrel: 200 rpm.

Example 5 Preparation Method of a Stent with a Drug (Ibuprofen)-Loaded Coating

A spraying method of drug-loaded micelles of an absorbable vascular stent coating for angiostenosis in an infant was provided, including the following steps:

S1: Preparation of drug-loaded coatings: S11: An absorbable vascular stent was washed with an acid to remove impurities on a surface of the absorbable vascular stent, then rinsed with UPW to remove the acid on the surface, vacuum-dried, and fixed on an automatic ultrasonic sprayer. S12: A polymer ibuprofen-loaded micellar solution was ultrasonically sprayed as a spraying solution uniformly on the surface of the absorbable vascular stent 7 times to obtain an absorbable vascular stent with ibuprofen-loaded coatings, where the ultrasonic spraying was conducted under the following conditions: ultrasonic power: 3.5 W, flow rate of a microsyringe pump: 4 mL/h, nitrogen pressure: 3.5 psi, and rotational speed of a rotating mandrel: 200 rpm.

S2: Preparation of blank coatings: S21: The absorbable vascular stent with ibuprofen-loaded coatings prepared in S1 was washed with an acid to remove impurities on a surface of the absorbable vascular stent, then rinsed with UPW to remove the acid on the surface, vacuum-dried, and fixed on an automatic ultrasonic sprayer. S22: A polymer blank micellar solution was loaded into a microsyringe pump and ultrasonically sprayed uniformly on the surface of the absorbable vascular stent with ibuprofen-loaded coatings prepared in S21 3 times to obtain an absorbable vascular stent with ibuprofen-loaded coatings and blank coatings, where the ultrasonic spraying was conducted under the following conditions: ultrasonic power: 3.5 W, flow rate of the microsyringe pump: 4 mL/h, nitrogen pressure: 3.5 psi, and rotational speed of a rotating mandrel: 200 rpm.

Example 6 Preparation Method of a Stent with Drug (RAPA+Ibuprofen)-Loaded Coatings A spraying method of drug-loaded micelles of an absorbable vascular stent coating for angiostenosis in an infant was provided, including the following steps:

S1: Preparation of drug-loaded coatings: S11: An absorbable vascular stent was washed with an acid to remove impurities on a surface of the absorbable vascular stent, then rinsed with UPW to remove the acid on the surface, vacuum-dried, and fixed on an automatic ultrasonic sprayer. S12: A polymer RAPA-loaded micellar solution was ultrasonically sprayed as a spraying solution uniformly on the surface of the absorbable vascular stent 4 times. S13: A polymer ibuprofen-loaded micellar solution was ultrasonically sprayed as a spraying solution uniformly on a surface of an absorbable vascular stent obtained in S12 3 times to obtain an absorbable vascular stent with RAPA-loaded coatings and ibuprofen-loaded coatings, where the ultrasonic spraying was conducted under the following conditions: ultrasonic power: 3.5 W, flow rate of a microsyringe pump: 4 mL/h, nitrogen pressure: 3.5 psi, and rotational speed of a rotating mandrel: 200 rpm.

S2: Preparation of blank coatings: S21: The absorbable vascular stent with RAPA-loaded coatings and ibuprofen-loaded coatings prepared in S1 was washed with an acid to remove impurities on a surface of the absorbable vascular stent, then rinsed with UPW to remove the acid on the surface, vacuum-dried, and fixed on an automatic ultrasonic sprayer. S22: A polymer blank micellar solution was loaded into a microsyringe pump and ultrasonically sprayed uniformly on the surface of the absorbable vascular stent with RAPA-loaded coatings and ibuprofen-loaded coatings prepared in S21 3 times to obtain an absorbable vascular stent with RAPA-loaded coatings, ibuprofen-loaded coatings, and blank coatings, where the ultrasonic spraying was conducted under the following conditions: ultrasonic power: 3.5 W, flow rate of the microsyringe pump: 4 mL/h, nitrogen pressure: 3.5 psi, and rotational speed of a rotating mandrel: 200 rpm.

The preferred specific examples of the present disclosure are described in detail above. It should be understood that a person of ordinary skill in the art can make various modifications and variations according to the concept of the present disclosure without creative efforts. Therefore, all technical solutions that can be obtained by a person skilled in the art based on the prior art through logical analysis, reasoning, or finite experiments according to the concept of the present disclosure shall fall within the protection scope defined by the appended claims.

What is claimed is:

1. A preparation method of a polymer drug-loaded micellar solution of an absorbable vascular stent coating for angiostenosis in an infant, comprising the following steps:
    S1: dissolving a drug to be encapsulated in an appropriate amount of an emulsifying agent, adding a chitosan-poly(p-dioxanone) amphiphilic block copolymer (chitosan-b-PPDO copolymer), and thoroughly mixing to obtain a drug-copolymer solution, wherein a mass ratio of the drug to be encapsulated to the chitosan-b-PPDO copolymer is 10:(20-60),
    S2: adding the drug-copolymer solution obtained in S1 dropwise to an emulsifying agent aqueous solution prepared in advance, and continuously stirring for 12 h to 36 h to obtain a stable drug-loaded micellar solution, wherein a mass ratio of an emulsifying agent to water in the emulsifying agent aqueous solution is 1:(0.5-2); a mass of the drug-copolymer solution is 2% to 10% of a mass of the emulsifying agent aqueous solution; and
    S3: removing the emulsifying agent from the stable drug-loaded micellar solution obtained in S2 through a vacuum evaporation, stirring a resulting concentrate for 2 h to 4 h, and centrifuging the resulting concentrate to obtain a supernatant; and filtering the supernatant to obtain a filtrate, and subjecting the filtrate to a dialysis to completely remove an unbound copolymer and a residual emulsifying agent to obtain the polymer drug-loaded micellar solution.

2. A preparation method of a polymer blank micellar solution of an absorbable vascular stent coating for angiostenosis in an infant, comprising the following steps:
    S1': dissolving a chitosan-b-PPDO copolymer in a small amount of an emulsifying agent to obtain a copolymer solution, adding the copolymer solution dropwise to an emulsifying agent aqueous solution prepared in advance, and continuously stirring for 12 h to 36 h to obtain a stable micellar solution, wherein a mass ratio of an emulsifying agent to water in the emulsifying agent aqueous solution is 1:(0.5-2); a mass of the copolymer solution is 2% to 10% of a mass of the emulsifying agent aqueous solution; and
    S2': removing the emulsifying agent from the stable micellar solution obtained in S1' through a vacuum evaporation, stirring a resulting concentrate for 2 h to 4 h, and centrifuging the resulting concentrate to obtain a supernatant; and filtering the supernatant to obtain a filtrate, and subjecting the filtrate to a dialysis to completely remove an unbound copolymer and a residual emulsifying agent to obtain the polymer blank micellar solution.

3. The preparation method of the polymer drug-loaded micellar solution of the absorbable vascular stent coating for angiostenosis in the infant according to claim 1, wherein in S1, the drug to be encapsulated is an anti-smooth muscle cell (SMC) proliferation drug and/or an anti-inflammatory drug.

4. The preparation method of the polymer drug-loaded micellar solution of the absorbable vascular stent coating for angiostenosis in the infant according to claim 3, wherein the anti-SMC proliferation drug is rapamycin (RAPA).

5. The preparation method of the polymer drug-loaded micellar solution of the absorbable vascular stent coating for angiostenosis in the infant according to claim 3, wherein the anti-inflammatory drug is ibuprofen.

6. The preparation method of the polymer drug-loaded micellar solution of the absorbable vascular stent coating for angiostenosis in the infant according to claim 1, wherein in S1, the chitosan-b-PPDO copolymer is shown in formula I:

wherein R is H or $OCH_3$; and $n_1$ and $n_2$ each are a positive integer, and $n_1:n_2=1:(10-20)$.

7. The preparation method according to claim 6, wherein a preparation method of the chitosan-b-PPDO copolymer comprises the following steps:

wherein R is H or OCH$_3$; and $n_1$ and $n_2$ each are a positive integer, and $n_1:n_2=1:(10\text{-}20)$.

8. The preparation method of the polymer drug-loaded micellar solution of the absorbable vascular stent coating for angiostenosis in the infant according to claim 1, wherein the emulsifying agent is selected from the group consisting of acetone, dichloromethane (DCM), and chloroform.

9. The preparation method of the polymer drug-loaded micellar solution of the absorbable vascular stent coating for angiostenosis in the infant according to claim 1, wherein in S3, the vacuum evaporation is conducted at a temperature of 160° C. to 170° C. and a pressure of 1 mmHg to 3 mmHg.

10. The preparation method of the polymer drug-loaded micellar solution of the absorbable vascular stent coating for angiostenosis in the infant according to claim 1, wherein in S3, the filtering is conducted with a microporous filter membrane.

11. The preparation method of the polymer drug-loaded micellar solution of the absorbable vascular stent coating for angiostenosis in the infant according to claim 1, wherein in S3, the dialysis is conducted by a dialysis bag with a molecular weight cut-off (MWCO) of 3,500 or more.

12. A spraying method of a micellar solution of an absorbable vascular stent coating for angiostenosis in an infant, comprising the following steps:
   S1: preparation of a drug-loaded coating: uniformly spraying the polymer drug-loaded micellar solution according to claim 1 as a spraying solution on a surface of an absorbable vascular stent by a first ultrasonic spraying process to obtain an absorbable vascular stent with the drug-loaded coating; and
   S2: preparation of a blank coating: uniformly spraying a polymer blank micellar solution as a spraying solution on a surface of the absorbable vascular stent with the drug-loaded coating by a second ultrasonic spraying process to obtain an absorbable vascular stent with the drug-loaded coating and the blank coating, wherein a ratio of a number of drug-loaded coatings to a number of blank coatings is 7:3, and the polymer blank micellar solution is prepared by a preparation method comprising the following steps:
   S1': dissolving a chitosan-b-PPDO copolymer in a small amount of an emulsifying agent to obtain a copolymer solution, adding the copolymer solution dropwise to an emulsifying agent aqueous solution prepared in advance, and continuously stirring for 12 h to 36 h to obtain a stable micellar solution, wherein a mass ratio of an emulsifying agent to water in the emulsifying agent aqueous solution is 1:(0.5-2); a mass of the copolymer solution is 2% to 10% of a mass of the emulsifying agent aqueous solution; and
   S2': removing the emulsifying agent from the stable micellar solution obtained in S1' through a vacuum evaporation, stirring a resulting concentrate for 2 h to 4 h, and centrifuging the resulting concentrate to obtain a supernatant; and filtering the supernatant to obtain a filtrate, and subjecting the filtrate to a dialysis to completely remove an unbound copolymer and a residual emulsifying agent to obtain the polymer blank micellar solution.

13. The spraying method according to claim 12, wherein the drug-loaded coating comprises an RAPA-loaded coating and/or an ibuprofen-loaded coating.

14. The spraying method according to claim 13, wherein the drug-loaded coating comprises the RAPA-loaded coating and the ibuprofen-loaded coating, and a ratio of a number of RAPA-loaded coatings to a number of ibuprofen-loaded coatings is 4:3.

15. The spraying method according to claim 12, wherein the first ultrasonic spraying process in S1 comprises:
   S11: washing the absorbable vascular stent with an acid to remove impurities on the surface of the absorbable vascular stent, rinsing the absorbable vascular stent with ultrapure water (UPW) to remove the acid on the surface, vacuum-drying the absorbable vascular stent, and fixing the absorbable vascular stent on an automatic ultrasonic sprayer; and
   S12: loading the polymer drug-loaded micellar solution into a microsyringe pump, and ultrasonically spraying the polymer drug-loaded micellar solution uniformly on the surface of the absorbable vascular stent to obtain the absorbable vascular stent with the drug-loaded coating, wherein the ultrasonically spraying is conducted under the following conditions: an ultrasonic power: 2 W to 5 W; a flow rate of the microsyringe pump: 3 mL/h to 5 mL/h; a nitrogen pressure: 2 psi to 5 psi; and a rotational speed of a rotating mandrel: 100 rpm to 300 rpm.

16. The spraying method according to claim 15, wherein S12 comprises:
- A: preparation of an RAPA-loaded coating: ultrasonically spraying a polymer RAPA-loaded micellar solution as a spraying solution uniformly on the surface of the absorbable vascular stent to obtain an absorbable vascular stent with the RAPA-loaded coating, wherein the ultrasonically spraying is conducted under the following conditions: the ultrasonic power: 2 W to 5 W; the flow rate of the microsyringe pump: 3 mL/h to 5 mL/h; the nitrogen pressure: 2 psi to 5 psi; and the rotational speed of the rotating mandrel: 100 rpm to 300 rpm; or
- B: preparation of an ibuprofen-loaded coating: ultrasonically spraying a polymer ibuprofen-loaded micellar solution as a spraying solution uniformly on the surface of the absorbable vascular stent to obtain an absorbable vascular stent with the ibuprofen-loaded coating, wherein the ultrasonically spraying is conducted under the following conditions: the ultrasonic power: 2 W to 5 W; the flow rate of the microsyringe pump: 3 mL/h to 5 mL/h and preferably 4 mL/h; the nitrogen pressure: 2 psi to 5 psi; and the rotational speed of the rotating mandrel: 100 rpm to 300 rpm; or
- C: preparation of an RAPA-loaded coating and an ibuprofen-loaded coating: ultrasonically spraying a polymer RAPA-loaded micellar solution as a spraying solution uniformly on the surface of the absorbable vascular stent, and ultrasonically spraying a polymer ibuprofen-loaded micellar solution as a spraying solution uniformly on a surface of an absorbable vascular stent with the RAPA-loaded coating to obtain an absorbable vascular stent with the RAPA-loaded coating and the ibuprofen-loaded coating in which a ratio of a number of RAPA-loaded coatings to a number of ibuprofen-loaded coatings is 4:3, wherein the ultrasonically spraying is conducted under the following conditions: the ultrasonic power: 2 W to 5 W; the flow rate of the microsyringe pump: 3 mL/h to 5 mL/h; the nitrogen pressure: 2 psi to 5 psi; and the rotational speed of the rotating mandrel: 100 rpm to 300 rpm.

17. The spraying method according to claim 12, wherein the second ultrasonic spraying process in S2 comprises:
- S21: washing the absorbable vascular stent with an acid to remove impurities on the surface of the absorbable vascular stent, rinsing the absorbable vascular stent with UPW to remove the acid on the surface, vacuum-drying the absorbable vascular stent, and fixing the absorbable vascular stent on an automatic ultrasonic sprayer; and
- S22: ultrasonically spraying the polymer blank micellar solution as a spraying solution uniformly on the surface of the absorbable vascular stent with the drug-loaded coating to obtain the absorbable vascular stent with the drug-loaded coating and the blank coating in which a ratio of a number of drug-loaded coatings to a number of blank coatings is 7:3, wherein the ultrasonically spraying is conducted under the following conditions: an ultrasonic power: 2 W to 5 W; a flow rate of the microsyringe pump: 3 mL/h to 5 mL/h; a nitrogen pressure: 2 psi to 5 psi; and a rotational speed of a rotating mandrel: 100 rpm to 300 rpm.

18. The preparation method of the polymer blank micellar solution of the absorbable vascular stent coating for angiostenosis in the infant according to claim 2, wherein in S1', the chitosan-b-PPDO copolymer is shown in formula I:

(I)

wherein R is H or $OCH_3$; and $n_1$ and $n_2$ each are a positive integer, and $n_1:n_2=1:(10-20)$.

* * * * *